United States Patent
Bastianelli et al.

(10) Patent No.: US 11,795,465 B2
(45) Date of Patent: Oct. 24, 2023

(54) MEIOTIC PROMOTORS AND USES THEREOF

(71) Applicants: MEIOGENIX, Paris (FR); Institut National De Recherche Pour L'Agriculture, L'Alimentation et L'Environnement, Paris (FR); UNIVERSITÉ CLAUDE BERNARD LYON 1, Villeurbanne (FR); CENTRE NATIONAL DE LA RECHERCHE SCIENTIFIQUE, Paris (FR); ECOLE NORMALE SUPERIEURE DE LYON, Lyons (FR)

(72) Inventors: Giacomo Bastianelli, Paris (FR); Alain Nicolas, Paris (FR); Peter Rogowsky, Lyons (FR)

(73) Assignees: MEIOGENIX, Paris (FR); INTITUT NATIONAL DE RECHERCHE POUR L'AGRICULTURE, L'ALIMENTATION ET L'ENVIRONNEMENT, Paris (FR); UNIVERSITE CLAUDE BERNARD LYON 1, Villeurbanne (FR); CENTRE NATIONAL DE LA RECHERCHE SCIENTIFIQUE, Paris (FR); ECOLE NORMALE SUPERIEURE DE LYON, Lyons (FR)

( * ) Notice: Subject to any disclaimer, the term of this patent is extended or adjusted under 35 U.S.C. 154(b) by 167 days.

(21) Appl. No.: 17/057,719

(22) PCT Filed: May 23, 2019

(86) PCT No.: PCT/EP2019/063377
§ 371 (c)(1),
(2) Date: Nov. 23, 2020

(87) PCT Pub. No.: WO2019/224324
PCT Pub. Date: Nov. 28, 2019

(65) Prior Publication Data
US 2021/0230619 A1    Jul. 29, 2021

(30) Foreign Application Priority Data
May 24, 2018 (FR) ...................... 1854405

(51) Int. Cl.
*C12N 15/82* (2006.01)
(52) U.S. Cl.
CPC .............................. *C12N 15/8222* (2013.01)
(58) Field of Classification Search
None
See application file for complete search history.

(56) References Cited

U.S. PATENT DOCUMENTS

2007/0130645 A1* 6/2007 Wu .................... C12N 15/8234
800/278

FOREIGN PATENT DOCUMENTS

| EP | 3 150 626 | 4/2017 |
| WO | WO 2015/001521 | 1/2015 |
| WO | WO 2017/161264 | 9/2017 |

OTHER PUBLICATIONS

Sequence Accession BEI68403, 2017. Sequence alignment is attached to the office action. (Year: 2017).*
Kim et al, Plant Mol Biol 24: 105-117, 1994 (Year: 1994).*
Benfey et al, Science 250: 959-966, 1990 (Year: 1990).*
Written Opinion in International Application No. PCT/EP2019/063377, dated Jun. 25, 2019, pp. 1-6.

* cited by examiner

*Primary Examiner* — Vinod Kumar
(74) *Attorney, Agent, or Firm* — SALIWANCHIK, LLOYD & EISENSCHENK (57) ABSTRACT

The present invention relates to new transcriptional promoters that are functional during meiosis. It thus provides new tools, methods and compositions for the expression of proteins during meiosis in a eukaryotic cell, and more particularly in a plant cell.

6 Claims, 3 Drawing Sheets
Specification includes a Sequence Listing.

tagggataacagggtaatctcatcttggtctttcgatagctgttcttgaactgaaaggatga
  Site I-SceI
tttgacaaataagtgaactactaaattgtacatctagtttctattaactcagcacaactcca
acatttgtctcttgtaaataactttcgcagtgctcctaattgtgttagttataatccacgaa
aaggattgtatgttgacaaggaacagataagacctaatgctagcaaattcacttctgaacat
cttaactcctaaaaaaattcgacttctcacgtaggtcaagaaaacctgaaccctgtca
catccatacaaagtgatattatagccatgtgagaacgacgggacggtccttagacctct
gcttactcagcttaaaattcgctccacgaggagtcgaatctatcctggtcactgaccagc
caagatgcagtgatacatgtcacttcaggcatgtagttacactttcagtttgaaacaatgg
aaatgatcctgtgtaaaattggcgctatcctgccattctatatacactgcaatgtggcga
atgcagtattggtggtgatgggagctgtgtaactgattgactcaatgtgcagGATTGTCCA
TCCAGCTCCAGGCGTTCCAGAGGCCCTGATACAGGAGATGTTCCAGCACAACCCAGGGGTGT
CCAGGGAGGGTCTCGGCCTGTACATAAGCCAGAAGCTGGTGAAAACGATGAGCGGCACGTTG
  Coding part of the last exon of ZmPHYC2
CAGTACCTACGAGAAGCCGACACCTCTTCGTTCATCATCCTGATAGAGTTCCCGGTCGCCCA
GCTCAGCAGCAAGCGGTCCAAGCCTTCGCCAAGTAAATTCTGAcactgatgctcctggaact
gcagtgacggttcggccgtgtcaaattctcgggtgtagggtgtacctctggccaagtgactg
atattctgaaaaacatacggactctagtataggagaagaggaatcctaatcctagtaatta
  3'UTR part of the last exon of ZmPHYC2
tatcttagtagatatgtcttagtctcttgttaattttttgtcttgagaggactatatatac
tgataaagtgataatttattcagagaataaagaatgggctccatgctttgtctatgtattct
cttcttgagggcaatttacgcctcttgagaagggtggcttcgttgtgggctcttgaaggcc
cacgcagtccaacggagcccactaagcctaattctgtttcttcgcgatcgattagctgatta
gctCcatggcggcttcgaaaaaatcaaaataaaaaactagcgccATGG (SEQ ID NO : 5)
 Point              5'UTR part of the first
 mutation           exon of ZmSpo11-1

MEIOTIC PROMOTORS AND USES THEREOF

CROSS-REFERENCE TO RELATED APPLICATION

This application is the U.S. national stage application of International Patent Application No. PCT/EP2019/063377, filed May 23, 2019.

The Sequence Listing for this application is labeled "2R46522.txt" which was created on Jan. 23, 2021 and is 7 KB. The entire content of the sequence listing is incorporated herein by reference in its entirety.

The present invention relates to tools, methods and compositions for the expression of proteins during meiosis in a eukaryotic cell, and more particularly in a plant cell.

TECHNOLOGICAL BACKGROUND OF THE INVENTION

In order to optimize plant production, the agricultural industry is perpetually searching for plants with improved characteristics, in particular with regard to growth, yield, organoleptic properties, resistance to disease or climatic variations, or with regard to characteristics of importance in green chemistry or for biofuel production.

Conventionally, a plant having particular properties can be obtained by sexual reproduction by crossing two parental strains having characteristics of interest and by selecting a hybrid strain providing the desired improvement. This method is, however, random and the selection step can lead to significant delays.

Alternatively, it can also be considered to genetically modify the plant by a recombinant DNA technology. This modification may nevertheless be a barrier to its use, whether for regulatory, health or environmental reasons.

A third alternative consists in causing a reassortment of the alleles of paternal and maternal origin in the genome, during meiotic recombination. Meiotic recombination is an exchange of DNA between homologous chromosomes during meiosis. It is initiated by the formation of double-strand breaks in either of the chromatids of the homologous chromosomes, followed by the repair of these breaks, using a chromatid of the homologous chromosome as a template. However, meiotic recombinations have the disadvantage of being distributed non-uniformly in terms of frequency and location along the chromosomes.

Recent years have seen the emergence of new technologies for influencing the frequency or positioning of meiotic recombinations. For example, it has been demonstrated that it is possible to modify the sites of double-strand break formation by expressing recombinant proteins during the prophase of the first meiotic division (Pecina et al, 2002 Cell, 111, 173-184; WO 2016/120480). These new tools open up extremely interesting prospects for directed optimization of plants via a reassortment of genes naturally present in the plant.

However, the modulation of meiotic events via the expression of recombinant proteins requires the use of promoters having transcriptional activity during this phase. Some of these promoters have been described, such as the *Arabidopsis thaliana* DMC1 gene promoter (Klimyuk and Jones. Plant J. 1997 January; 11(1):1-14) or the *Saccharomyces cerevisiae* SPO13 gene promoter (Buckingham et al., Proc Natl Acad Sci USA. 1990 December; 87(23):9406-10). However, the available choice remains largely inadequate to cover all the applications envisaged. There is thus a real need for new transcriptional promoters for the expression of proteins of interest during meiosis.

SUMMARY OF THE INVENTION

The present invention proposes a novel transcriptional promoter that is functional during meiosis. Thus, according to a first aspect, it relates to an isolated nucleic acid having a functional transcriptional promoter activity during meiosis and comprising, or consisting of, a nucleotide sequence selected from the group consisting of the sequence SEQ ID NO: 1 and functional variants thereof, said functional variants comprising, or consisting of, a sequence having at least 70% identity with the sequence SEQ ID NO: 1;
a fragment of the sequence SEQ ID NO: 1 of at least 50 consecutive nucleotides, or
a sequence capable of hybridizing under conditions of low, moderate or high stringency with the sequence SEQ ID NO: 1 or its complementary strand.

Preferably, the nucleic acid according to the invention comprises, or consists of, a nucleotide sequence selected from the group consisting of the sequence SEQ ID NO: 1 and functional variants thereof having at least 80% identity with the sequence SEQ ID NO: 1. In particular, it may comprise, or consist of, a nucleotide sequence selected from the group consisting of the sequences SEQ ID NO: 1, 2, 3 or 4.

According to another aspect, the present invention relates to an expression cassette comprising a coding sequence operably linked to a nucleic acid according to the invention. It also relates to an expression vector comprising a nucleic acid or an expression cassette according to the invention.

The coding sequence may in particular encode a polypeptide of interest, preferably a reporter protein or a protein capable of modulating, preferably increasing, the frequency of meiotic recombinations, a protein that modifies the structure of chromatin such as for example histone (de)acetylases or histone (de)methylases or a protein that modifies the methylation of DNA. Alternatively, the coding sequence encodes a nucleic acid of interest, preferably an siRNA, an shRNA, an RNAi, an miRNA, an antisense RNA, a ribozyme, a DNAzyme or a guide RNA capable of targeting the action of a CRISPR-type endonuclease, preferably Cas9 or dCas9, to a specific sequence.

According to another aspect, the present invention also relates to a non-human host cell transfected or transformed with a nucleic acid, an expression cassette or an expression vector according to the invention.

In still another aspect, the invention relates to a process, preferably an in vitro process, for expressing a coding sequence of interest in a non-human host cell during meiosis, comprising the introduction into said cell of a nucleic acid, an expression cassette or an expression vector according to the invention, preferably an expression cassette or an expression vector according to the invention, said coding sequence being operably linked to a nucleic acid according to the invention. It also relates to a process, preferably an in vitro process, for producing a multicellular plant organism expressing a coding sequence of interest during meiosis, comprising the introduction into a plant cell of a nucleic acid, an expression cassette or an expression vector according to the invention, preferably an expression cassette or an expression vector according to the invention, said coding sequence being operably linked to a nucleic acid according to the invention, and the reconstitution of said organism from said cell. Preferably the host cell is a plant cell.

The present invention also relates to a multicellular plant organism comprising an expression cassette or an expression vector according to the invention, as well as the use of a nucleic acid, an expression cassette or an expression vector according to the invention to express a coding sequence of interest, preferably heterologous, in a non-human host cell, preferably a plant cell, during meiosis.

DETAILED DESCRIPTION OF THE INVENTION

The present application describes the identification and characterization of regulatory nucleic acid sequences of plant origin which make it possible to control the expression of a gene of interest in a eukaryotic cell, preferably a plant cell, during meiosis. Indeed, the inventors have identified a nucleotide sequence upstream of the ZmSpo11-1 gene (GeneID NCBI: 100279325) from maize (*Zea mays*) having transcriptional promoter activity during meiosis. They also demonstrated that this promoter performed better during meiosis than a strong constitutive promoter such as the ubiquitin promoter (ZmUBI).

Definitions

In the present description, the terms "nucleic acid", "nucleic sequence", "polynucleotide", "oligonucleotide", "nucleotide sequence" are used interchangeably and refer to a polymer of deoxyribonucleotides and/or ribonucleotides. These terms may in particular comprise synthetic or semi-synthetic, recombinant molecules comprising non-natural bases or modified nucleotides comprising for example a modified bond, a modified purine or pyrimidine base, or a modified sugar. The nucleic acid according to the invention may be obtained by any method known to the person skilled in the art, for example by chemical synthesis and/or recombination and/or mutagenesis techniques. According to certain preferred embodiments, the nucleic acid according to the invention is a DNA molecule, preferably a double-stranded DNA molecule. This molecule can be obtained by recombinant techniques well known to the skilled person.

As used herein, the term "isolated" refers to biological material that has been removed from its natural environment. More particularly, the term "isolated nucleic acid" refers to a nucleic acid molecule that is separated from the nucleic acids adjacent to it when it is in its natural environment, i.e., in the genome from which it was isolated. The isolated nucleic acid may be comprised in a vector, a genome, a composition or any other element, while remaining isolated, insofar as this element does not constitute its natural environment.

As used herein, the term "transcriptional promoter" refers to a regulatory element that has the ability to initiate transcription of a nucleic acid to which it is operably linked. The activity of such a promoter can be evaluated by any method known to the skilled person, and in particular by any method for quantifying the mRNA or protein obtained from the gene controlled by the promoter. By way of illustration, the activity can be measured by evaluating the amount of mRNA, for example by Northern blot or RT-PCR, or by evaluating the amount of translated protein, for example by Western blot, ELISA, colorimetric tests, enzyme activity tests or by using a reporter gene system.

As used herein, the term "operably linked" refers to nucleotide sequences that are combined/arranged in such a way that the function of one acts on the other. Thus, a transcriptional promoter and a nucleotide sequence, such as a coding sequence, are operably linked when the expression of the nucleotide sequence is controlled by said promoter.

The term "% sequence identity" or "% identity", as used herein, refers to the percentage of identical nucleotides in an alignment of two polynucleotides. This percentage can be easily calculated by the skilled person using a sequence comparison computer program. Sequence identity is determined by comparing the sequences after they have been aligned by maximizing overlaps and identities while minimizing spaces. In particular, sequence identity can be determined using one of the global or local mathematical alignment algorithms available. Sequences of similar size are preferably aligned using a global alignment algorithm (e.g. Needleman and Wunsch, 1970) that optimally aligns sequences along their entire length. Sequences of substantially different lengths are preferably aligned using a local alignment algorithm (e.g. Smith and Waterman, 1981; Altschul et al., 1997; Altschul et al., 2005). Alignments to determine percent identity can be performed by any method known to the skilled person, in particular using computer programs available on the internet (for example, blast.ncbi.nlm.nih.gov/ or Worldwide Website: ebi.ac.uk/Tools/emboss/). Preferably, the value of the percent identity refers here to a value obtained with the EMBOSS Needle program which uses the Needleman-Wunsch global alignment algorithm with the default parameters, namely: Scoring matrix=BLOSUM62, Gap open=10, Gap extend=0.5, End gap penalty=false, End gap open=10 and End gap extend=0.5.

According to a first aspect, the present application relates to a nucleic acid, preferably isolated, having a functional transcriptional promoter activity during meiosis and comprising, or consisting of, a nucleotide sequence selected from the group consisting of the sequence SEQ ID NO: 1 and functional variants thereof.

The nucleic acid according to the invention has a functional transcriptional promoter activity during meiosis. This means that it is capable of initiating, during meiosis, the transcription of a nucleic acid to which it is operably linked.

Meiosis comprises two successive cell divisions. The first meiotic division is called reductional and comprises the steps of prophase I, metaphase I, anaphase I and telophase I. The second meiotic division is called equational and comprises the steps of metaphase II, anaphase II and telophase II. Preferably, the nucleic acid according to the invention has a functional transcriptional promoter activity at least during prophase I of meiosis.

According to a preferred embodiment, the nucleic acid according to the invention has a transcriptional promoter activity during meiosis, and more particularly during prophase I of meiosis, which is superior to that of a strong constitutive promoter. Preferably, the nucleic acid according to the invention has a transcriptional promoter activity during meiosis that is superior to that of the promoter of the ubiquitin gene, and in particular of the maize ubiquitin gene (GenBank accession number: 594464, position 4-1997). The nucleic acid according to the invention is therefore preferably capable of inducing, during meiosis, and more particularly during prophase I of meiosis, the expression of a coding sequence of interest more efficiently than a strong constitutive promoter, in particular that of the promoter of the ubiquitin gene, and in particular of the maize ubiquitin gene. This characteristic can be evaluated by any method known to the skilled person, and in particular according to the method described in the experimental part below. According to an embodiment, the nucleic acid according to the invention comprises, or consists of, the sequence SEQ ID NO: 1.

According to another embodiment, the nucleic acid according to the invention comprises, or consists of, a functional variant of the sequence SEQ ID NO: 1.

As used herein, the term "variant" refers to a nucleotide sequence that differs from the parent sequence (e.g. SEQ ID NO: 1) but that retains its essential properties. The sequence of the variant may differ from the parent sequence by one or more substitutions, deletions and/or insertions. The variant may have a length identical to or different from (shorter or longer than) the parent sequence. The term "functional variant" refers to a variant as defined above that retains the activity of the parent application, in this case a functional transcriptional promoter activity during meiosis.

According to an embodiment, the nucleic acid according to the invention comprises, or consists of, a functional variant of the sequence SEQ ID NO: 1 selected from the group consisting of
a sequence having at least 70%, preferably at least 80%, identity with the sequence SEQ ID NO: 1;
a fragment of the sequence SEQ ID NO: 1 of at least 50 consecutive nucleotides, and
a sequence capable of hybridizing under conditions of low, moderate or high stringency with the sequence SEQ ID NO: 1 or its complementary strand.

According to an embodiment, the nucleic acid according to the invention comprises, or consists of, a functional variant having a sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity with the sequence SEQ ID NO: 1, preferably over the entire length of the sequence SEQ ID NO: 1. The nucleic acid according to the invention may differ from the sequence SEQ ID NO: 1 by a maximum of 15, i.e. 1, 2, 3, 4, 5, 6, 7, 8, 9, 10, 11, 12, 13, 14 or 15, substitutions, insertions and/or deletions.

According to another particular embodiment, the nucleic acid according to the invention comprises, or consists of, a functional variant which is a fragment of the sequence SEQ ID NO: 1 of at least 50, 60, 70, 80, 90, 100, 110, 120, 130, 140, 150, 160 or 170 consecutive nucleotides. Preferably, the functional variant is a fragment of the sequence SEQ ID NO: 1 of at least 100 consecutive nucleotides. More particularly preferably, the functional variant is a fragment of the sequence SEQ ID NO: 1 of at least 110 consecutive nucleotides.

According to another particular embodiment, the nucleic acid according to the invention comprises, or consists of, a functional variant having a sequence capable of hybridizing under conditions of low, moderate or high stringency with the sequence SEQ ID NO: 1 or its complementary strand, preferably under conditions of moderate or high stringency, and more particularly preferably under conditions of high stringency.

As used herein, the term "conditions of low stringency" refers to a pre-hybridization and a hybridization at 42° C. in medium containing 5×SSPE, 0.3% SDS, 200 μg/mL denatured and sonicated salmon sperm DNA and 25% formamide, followed by conventional Southern blot procedures for 12 to 24 hours. The medium is then washed three times for 15 minutes in 2×SSC, 0.2% SDS buffer at 50° C. As used herein, the term "conditions of moderate stringency" refers to pre-hybridization and hybridization at 42° C. in medium containing 5×SSPE, 0.3% SDS, 200 μg/mL denatured and sonicated salmon sperm DNA and 35% formamide, followed by conventional Southern blot procedures for 12 to 24 hours. The medium is then washed three times for 15 minutes in 2×SSC, 0.2% SDS buffer at 55° C. As used herein, the term "conditions of high stringency" refers to pre-hybridization and hybridization at 42° C. in medium containing 5×SSPE, 0.3% SDS, 200 μg/mL denatured and sonicated salmon sperm DNA and 50% formamide, followed by standard Southern blot procedures for 12 to 24 hours. The medium is then washed three times for 15 minutes in 2×SSC, 0.2% SDS buffer at 65° C.

According to preferred embodiments, the functional variants of the sequence SEQ ID NO: 1 comprise, preferably when aligned with SEQ ID NO: 1 by means of a global or local mathematical alignment algorithm, at least 1, 2 or 3 retained motifs selected from the following motifs:
TTGN[A/T]GG, preferably TTGNAGG, and particularly preferably TTGAAGG, at positions 62 to 68 of SEQ ID NO: 1,
CGANCGA, preferably CGATCGA, at positions 115 to 121 of SEQ ID NO: 1,
AAGCCNA, preferably AAGCCTA, at positions 94 to 100 of SEQ ID NO: 1, and
AAAANNAAAA (SEQ ID NO: 7), preferably AAAATCAAAA (SEQ ID NO: 8), at positions 152 to 161 of SEQ ID NO: 1.
N can be A, T, C or G.
Preferably, the functional variants comprise these 4 conserved motifs. These motifs are framed in FIG. 1.

The nucleic acid according to the invention comprises, or consists of, a nucleotide sequence selected from the group consisting of the sequences SEQ ID NO: 2, 3 or 4 and functional variants thereof, provided that these functional variants comprise (i) at least 50, at least 60, at least 70, at least 80, at least 90, at least 100, at least 110, at least 120, at least 130, at least 140, at least 150, at least 160 or at least 170 consecutive nucleotides of SEQ ID NO: 1, and/or (ii)

comprise a sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity with the sequence SEQ ID NO: 1. Preferably, the functional variants comprise at least 1, 2 or 3 of the above-mentioned conserved motifs, preferably all 4 motifs.

According to another particular embodiment, the nucleic acid according to the invention comprises, or consists of, a nucleotide sequence selected from the group consisting of the sequences SEQ ID NO: 2, 3 or 4 and functional variants thereof, provided that these functional variants comprise (i) at least 110 consecutive nucleotides of SEQ ID NO: 1, and/or (ii) comprise a sequence having at least 70% identity with the sequence SEQ ID NO: 1, preferably at least 70% sequence identity over the entire length of the sequence SEQ ID NO: 1. Preferably, the functional variants comprise at least 1, 2 or 3 of the above-mentioned conserved motifs, preferably all 4 motifs.

According to a preferred embodiment, the nucleic acid according to the invention comprises, or consists of, a nucleotide sequence selected from the group consisting of the sequence SEQ ID NO: 1 and functional variants thereof having at least 80% identity with the sequence SEQ ID NO: 1, preferably at least 80% sequence identity over the entire length of the sequence SEQ ID NO: 1.

In a second aspect, the present invention also relates to an expression cassette comprising a coding sequence of interest operably linked to a nucleic acid according to the invention.

As used herein, the term "expression cassette" refers to a nucleic acid construct comprising a coding sequence and one or more control sequences required for the expression of said coding sequence. In particular, one of these control sequences is a nucleic acid according to the invention having promoter activity. In general, the expression cassette comprises a coding sequence and control sequences preceding (5' non-coding sequences) and following (3' non-coding sequences) the coding sequence which is required for the expression of the gene product of interest. Thus, an expression cassette typically comprises a promoter sequence, an untranslated 5' region, a coding sequence and an untranslated 3' region that typically contains a polyadenylation site and/or a transcription terminator. The expression cassette may also comprise additional regulatory elements such as, for example, amplifying sequences (enhancers), a polylinker sequence facilitating the insertion of a DNA fragment into a vector and/or splicing signals. The expression cassette is typically included in a vector, to facilitate cloning and transformation.

Preferably, the expression cassette is a recombinant expression cassette, i.e. the nucleic acid according to the invention is functionally linked to a heterologous coding sequence. As used herein, the term "heterologous" refers to a coding sequence that is different from that to which the promoter is functionally linked in a natural genome. In particular, in certain preferred embodiments, the coding sequence of interest is not the maize (*Zea mays*) ZmSpo11-1 gene (GeneID: 100279325).

The coding sequence of interest operably linked to a nucleic acid according to the invention can encode a polypeptide of interest or a nucleic acid of interest.

According to an embodiment, the coding sequence of interest operably linked to a nucleic acid according to the invention encodes a polypeptide of interest. The polypeptide of interest may be any polypeptide the expression of which is desired during meiosis. In particular, the polypeptide of interest may be a reporter protein, a protein capable of modulating, preferably increasing, the frequency of meiotic recombinations, a protein that modifies the structure of chromatin such as for example histone (de)acetylases or histone (de)methylases, and/or a protein that modifies DNA methylation.

The reporter protein can be easily chosen by the skilled person according to the nature of the host cell and the detection technique. The reporter protein can be chosen, for example, from fluorescent proteins, alkaline phosphatases, beta-glucuronidases, beta-galactosidases, beta-lactamases or horseradish peroxidase.

The protein capable of modulating the frequency of meiotic recombinations can also be easily chosen by the skilled person. The modulation can be a general increase in the frequency of recombinations or a targeted increase, i.e. an increase concerning a given genomic region. By way of example, this protein can be a protein obtained by fusing an Spo11 protein with a DNA-binding domain such as the Gal4 transcription activator (Pecina et al, 2002 Cell, 111, 173-184), the zinc finger (ZF) domain or the transcription activator-like effector (TALE) domain, or a protein obtained by fusing an Spo11 protein with a Cas9 domain, preferably a dead Cas9 (dCas9) domain lacking nuclease activity, and used in combination with a guide RNA capable of targeting a specific sequence (WO 2016/120480).

According to another embodiment, the coding sequence of interest operably linked to a nucleic acid according to the invention encodes a nucleic acid of interest. The nucleic acid of interest may be any nucleic acid the expression of which is desired during meiosis. In particular, the nucleic acid of interest may be an siRNA, an shRNA, an RNAi, an miRNA, an antisense RNA, a ribozyme, a DNAzyme or a guide RNA capable of targeting the action of a CRISPR-type endonuclease, preferably Cas9 or dCas9, at the level of a specific sequence.

The coding sequence of interest operably linked to a nucleic acid according to the invention may encode one or more molecules of interest, i.e. for one or more polypeptides of interest and/or one or more nucleic acids of interest.

The expression cassette according to the invention may comprise one or more coding sequences of interest operably linked to the nucleic acid according to the invention.

All the embodiments concerning the other aspects of the invention are also envisaged in this aspect.

In a third aspect, the present invention also relates to a vector comprising a nucleic acid according to the invention or an expression cassette according to the invention.

As used herein, the term "vector" refers to a nucleic acid molecule used as a vehicle to transfer genetic material, and in particular to deliver a nucleic acid into a host cell, either in vitro or in vivo. The vector may be DNA or RNA, circular or non-circular, single- or double-stranded. Vectors comprise, but are not limited to, plasmids, phasmids, cosmids, transposable elements, viruses and artificial chromosomes (for example YACs). Vectors can be constructed using classical molecular biology techniques well known to the skilled person.

Advantageously, the vector according to the invention is a plant vector, i.e. a vector capable of transforming a plant cell. Examples of plant vectors are described in the literature, among which particular mention may be made of the T-DNA plasmids of *A. tumefaciens* pBIN19 (Bevan et al., 1984, Nucleic Acids Research, vol. 12: 8711-8721), the vector pPZP100 (Hajdukiewicz et al. 1994, Plant Mol. Biol. 25: 989-994), the pCAMBIA series vectors (R. Jefferson, 1987, Plant Mol. Biol. Rep. 5:387-405) or the vectors described in the papers by Karimi et al. (Plant Physiology; 2007, 145(4): 1183-91, and Plant Physiology; 2007, 145(4): 1144-54) which are more specific to monocots.

The vectors according to the invention may further comprise one or more bacterial and/or eukaryotic origins of replication. It may in particular comprise a bacterial origin of replication allowing its selection during cloning steps, for example an origin of replication functional in *E. coli*, and another origin of replication used during transfer into the plant cell, for example an origin of replication functional in *Agrobacterium tumefaciens*. The vector may further comprise elements allowing its selection in a bacterial or eukaryotic host cell such as, for example, an antibiotic resistance gene, a gene to complement an auxotrophy or an herbicide tolerance gene. Such elements are well known to the skilled person and widely described in the literature.

The expression vector may also comprise one or more sequences allowing the targeted insertion of the vector, the expression cassette or the nucleic acid according to the invention into the genome of a host cell.

All the embodiments concerning the other aspects of the invention are also envisaged in this aspect.

In another aspect, the present invention relates to the use of a nucleic acid, an expression cassette or an expression vector according to the invention to transform or transfect a host cell. It also relates to a host cell transformed or transfected by at least one nucleic acid, expression cassette or expression vector according to the invention. Preferably, the transformed or transfected host cell contains said nucleic acid, said cassette or said vector according to the invention in a non-integrated form or integrated into the genome.

As used herein, the term "host cell" refers to a prokaryotic cell or a non-human eukaryotic cell. Preferably, the host cell is a non-human eukaryotic cell selected from a yeast, plant, fungus or animal cell. More particularly preferably, the host cell is a plant cell. According to certain embodiments, this term also includes plant protoplasts.

In a preferred embodiment, the host cell is a plant cell. In particular, the host cell can be a plant cell selected from the group consisting of cereals such as maize, rice, wheat, barley, sorghum, millet, oats and rye, sunflower, rapeseed, model plants such as *Arabidopsis thaliana* or *Brachypodium distachyon*, vegetables such as tomato, bell pepper, chili, cabbage, cauliflower or lettuce, legumes such as broad beans, lentils, split peas, chickpeas, soybeans, fava beans or alfalfa, cotton, sugar plants such as sugar cane or beets, and fruit plants such as citrus producing plants (for example, lemons, oranges or grapefruit), berries (for example, strawberries, currants, raspberries or grapes), pome fruits (for example, apples or pears), stone fruits (for example, apricots, cherries or peaches) or nuts (for example, hazelnuts or walnuts). More particularly preferably, the host cell is a maize cell.

The host cell can be transiently or stably transformed/transfected. The nucleic acid, cassette or vector according to the invention may be contained in the cell in a non-integrated form or integrated into the genome.

Host cell transfection or transformation techniques are well known to the skilled person. In particular, plant transgenesis techniques are well known and comprise for example the use of the bacterium *Agrobacterium tumefaciens*, electroporation, direct transfer, biolistic techniques, etc.

A commonly used technique is based on the use of *Agrobacterium tumefaciens*, which essentially consists of introducing the construct of interest (nucleic acid, cassette, vector, etc.) into *A. tumefaciens* and then contacting this transformed bacterium with appropriate explants of the chosen plant. The introduction of the expression cassette into the bacterium is typically performed using a plasmid with a disarmed T-DNA as vector, which can be transferred into the bacterium, for example, by thermal shock. Incubation of the transformed bacterium with appropriate explants results in the transfer of the T-DNA containing the expression cassette into the genome of the disc cells. These can eventually be grown under appropriate conditions to reconstitute a transgenic plant whose cells comprise the construction of the invention. For more details or variants of the implementation of the *A. tumefaciens* transformation technique, it is possible to refer for example to Horsch et al., (1985) Science 227:1229-1231, Hooykaas and Schilperoort (1992) Plant Mol. Biol. 19:15-38 or Ishida et al. (2007) Nat Protoc, 2(7):1614-21.

Another plant transformation technique is based on the firing of microparticles (typically microbeads) to which the genetic constructs are attached, directly into plant cells, followed by the cultivation of these cells to reconstitute a transgenic plant. The particles used are typically gold particles, which are typically fired by means of a particle gun (see in particular Russell et al., In Vitro Cell. Dev. Biol. 1992, 28P, pp. 97-105 and Klein et al. Plant Physiol. 1989 September; 91(1):440-4).

The microinjection technique essentially consists of injecting genetic constructs into plant embryos or protoplasts and then cultivating these tissues in order to regenerate whole plants. Other plant transgenesis techniques are well known, or other protocols implementing the above techniques are described in the prior art (Siemens, J and Schieder, 1996, Plant Tiss. Cult. Biotechnol. 2:66-75) and can be applied to the present invention.

All the embodiments concerning the other aspects of the invention are also envisaged in this aspect.

In another aspect, the present invention relates to a process for expressing a coding sequence of interest in a host cell during meiosis, comprising the introduction into said cell of a nucleic acid, an expression cassette or an expression vector according to the invention, said coding sequence being operably linked to a nucleic acid according to the invention. It also relates to the use of a nucleic acid, an expression cassette or an expression vector according to the invention to express a coding sequence of interest, preferably heterologous, in a host cell during meiosis.

The coding sequence of interest may be heterologous with respect to the promoter, i.e. different from that to which the promoter is functionally linked in a natural genome, and/or heterologous with respect to the host cell, i.e. a sequence that is not naturally present in the host cell. Preferably, the coding sequence of interest is heterologous with respect to the promoter, and optionally heterologous with respect to the host cell.

The coding sequence of interest is either comprised in the expression cassette or expression vector according to the invention and is operably linked to a nucleic acid according to the invention, or is already present in the host cell genome. In the latter case, the nucleic acid according to the invention is inserted into the genome of the cell so as to be operably linked to said sequence and thus allow its expression during meiosis.

All the embodiments concerning the other aspects of the invention are also envisaged in this aspect.

According to still another aspect, the present invention relates to a multicellular plant organism, comprising an expression cassette or a vector according to the invention. It also relates to a process for producing a multicellular plant organism expressing a coding sequence of interest during meiosis, comprising the introduction into a plant cell of a nucleic acid, an expression cassette or a vector according to the invention, preferably an expression cassette or a vector according to the invention, said coding sequence being operably linked to a nucleic acid according to the invention, and the reconstitution of said organism from said cell. Preferably, the coding sequence of interest is heterologous with respect to the promoter, and optionally heterologous with respect to the plant cell.

Optionally, the process may also comprise a step of selecting the organisms containing the nucleic acid, cassette or vector according to the invention. This selection may be carried out by any method known to the skilled person, in particular by DNA amplification methods using primers targeting a specific sequence of the nucleic acid, cassette or vector.

The process may also further comprise a step of crossing the organisms obtained among themselves or with other plants of the same species or of different species. At the end of this crossing, it is possible to select organisms containing the nucleic acid, cassette or vector according to the invention.

The introduction of the nucleic acid, cassette or vector according to the invention into the cell may be carried out by any means known to the skilled person, for example by one of the methods described above.

As used herein, the term "multicellular plant organism" refers to a whole plant, plant parts such as flowers, seeds, leaves, stems, fruits, pollen, tubers, wood, or multicellular structures such as calluses, plant organs, especially meiotic panicles and meiotic spikelets, or immature embryos (e.g. explants used for transgenesis). In certain preferred embodiments, the multicellular plant organism is a whole plant or a seed.

The reconstitution of a multicellular plant organism as defined above from a transfected or transformed plant cell uses routine techniques well known to the skilled person.

All the embodiments concerning the other aspects of the invention are also envisaged in this aspect.

The processes according to the invention may be in vitro, in vivo or ex vivo processes. Preferably, the processes according to the invention are in vitro processes.

The following examples are presented for illustrative and non-limiting purposes.

Examples

The inventors identified a transcriptional promoter that is functional during meiosis and demonstrated that the use of this promoter allowed the expression of a fusion protein comprising a ZmSpo11-1 domain and a DNA-binding domain during meiosis.

The ZmSpo11-1 gene carries the identifier GRMZM2G129913_T04 (gene model T04 of the GRMZM2G129913 gene) in version 3 of the reference sequence of the B73 maize genotype. In the genome of this genotype, the ZmPHYC2 gene (GRMZM2G129889_T01) is unusually close to ZmSpo11-1, with only 162 bp between the end of the predicted 3'UTR of ZmPHYC2 and the beginning of the predicted 5'UTR of ZmSpo11-1. To facilitate cloning of the promoter region, an internal NcoI restriction site was eliminated by point mutation, maintaining a single NcoI site at the 3' end of the fragment, which overlaps the START codon of ZmSpo11-1. At the 5' end an I-SceI restriction site has been added. The sequence used in the cloning described below and including the ZmSpo11-1 promoter is presented in FIG. 1.

A phylogenetic analysis involving several cereal species, namely *Zea mays, Sorghum bicolor, Setaria italica, Oryza sativa japonica, Brachypodium distachyon, Triticum aestivum, Saccharum officinarum* and *Hordeum vulgare*, revealed a strong sequence divergence in the intergenic region and the presence in this region of four conserved motifs, namely TTGX[A/T]GG, CGAXCGA, AAGCCXA and AAAAXXAAAA (SEQ ID NO: 7). These motifs are framed in FIG. 1.

Plasmid Constructions

A cassette comprising the chimeric TAL-ZmSpo11-1 gene under the control of the ZmSpo11-1 promoter contained in SEQ ID NO: 5 (FIG. 1) was inserted into a plasmid to obtain plasmid L1605. The TAL domain is a DNA-binding domain that has been designed to recognize the sequence 5'-TGGTTCTGTGACTACAAGTACAATG-3' (SEQ ID NO: 6). Its coding sequence was phased upstream of the ZmSpo11-1 cDNA, with a 36 bp spacer without a STOP codon making the linkage. An 18 bp sequence coding for a 6-His tag was phase-added at the end of the ZmSpo11-1 gene just before the STOP codon.

A plasmid L1604 was similarly obtained and contained a cassette comprising the chimeric TAL-ZmSpo11-1 gene under the control of the strong constitutive promoter of the maize ubiquitin gene, ZmUBI (GenBank accession number: S94464). Plasmid L1604 is identical to plasmid L1605 with the exception of the ZmUBI promoter which replaces the ZmSpo11-1 promoter.

Mutant Zmspo11-1

The inventors used a maize plant comprising a mutation consisting of a deletion of part of the ZmSpo11-1 gene (provided by Arnaud Ronceret). This mutant has a number of defects in recombination, chromosome pairing and synapses during meiosis and shows complete male and almost complete female sterility.

Male flowering and pollen production of heterozygous and homozygous plants for this deletion were characterized in terms of the panicle, the anther and the pollen.

Figure 2:
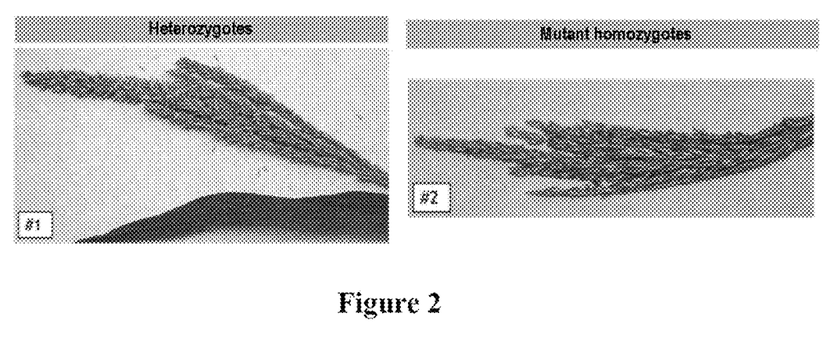
FIG. 2: Panicles. The panicles of homozygous mutant Zmspo11-1 plants carry far fewer anthers.
Figure 3:
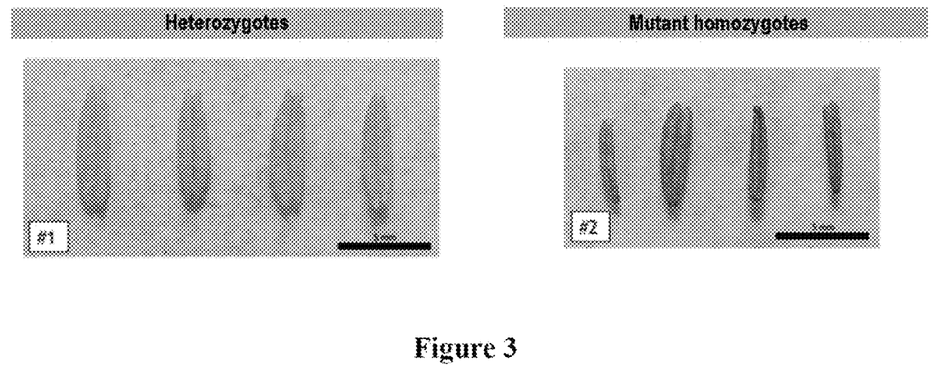
FIG. 3: Anthers. The anthers of homozygous mutant Zmspo11-1 plants are atrophied.
Figure 4:
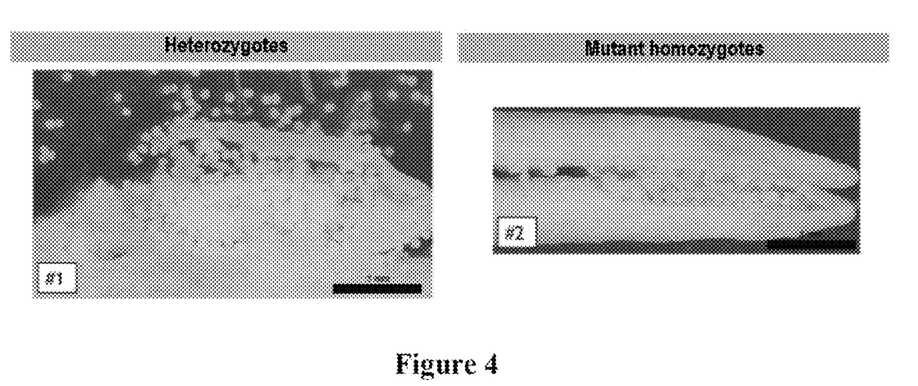
FIG. 4: Pollen. The anthers of homozygous mutant Zmspo11-1 plants contain many aborted pollen grains and nearly no turgid pollen grains.

It was thus shown that the panicles of the mutant plants carry far fewer anthers, and that the anthers of the mutant plants are atrophied and contain many aborted pollen grains and virtually no turgid pollen grains (FIGS. 2 to 4).

Transgenic Plants Containing the ZmSpo11-1 Promoter

Maize genotype A188 was transformed with plasmids L1604 and L1605 according to the standard protocol of Ishida et al (Nat Protoc. 2007; 2(7):1614-21).

For each construction, a single transformation event was obtained, each time represented by two plants from the same cal. T0 plants comprising either plasmid L1604 (ZmUBI promoter) or plasmid L1605 (ZmSpo11-1 promoter) were crossed with the mutant Zmspo11-1.

Complementation of the Zmspo11-1 Mutant

To test the complementation of the Zmspo11-1 mutant by transgenes L1604 (ZmUBI promoter-TAL-ZmSpo11-1 fusion protein) or L1605 (ZmSpo11-1 promoter-TAL-ZmSpo11-1 fusion protein), T0 plants were crossed with heterozygous plants carrying the Zmspo11-1 mutation.

T1 seedlings from these crosses were genotyped to identify seedlings carrying both the transgene and the mutation. Plants hemizygous for the transgene and hemizygous for the Zmspo11-1 mutation were self-fertilized.

T2 seedlings from self-fertilization were genotyped. Seedlings homozygous for the Zmspo11-1 mutation and (i) carrying transgene L1604 (ZmUBI promoter-TAL-ZmSpo11-1 fusion protein), (ii) carrying transgene L1605 (ZmSpo11-1 promoter-TAL-ZmSpo11-1 fusion protein), or (iii) not carrying a transgene, were selected for phenotypic analysis.

Figure 5:
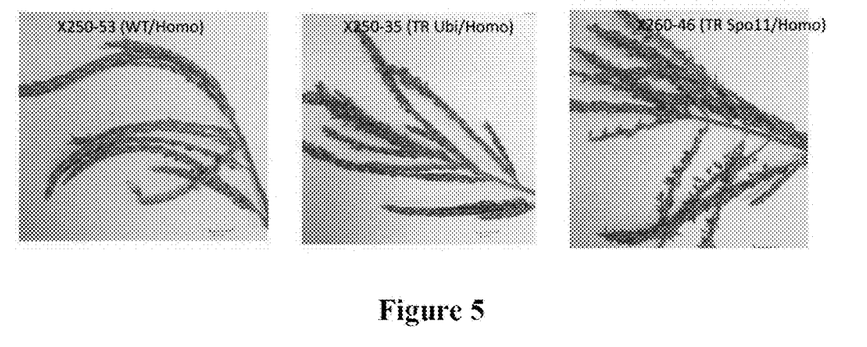
FIG. 5: Panicles. Panicles of homozygous mutant Zmspo11-1 (WT/Homo) plants supplemented by transgene L1605 (TR Spo11/Homo) or transgene L1604 (TR Ubi/Homo).
Figure 6:
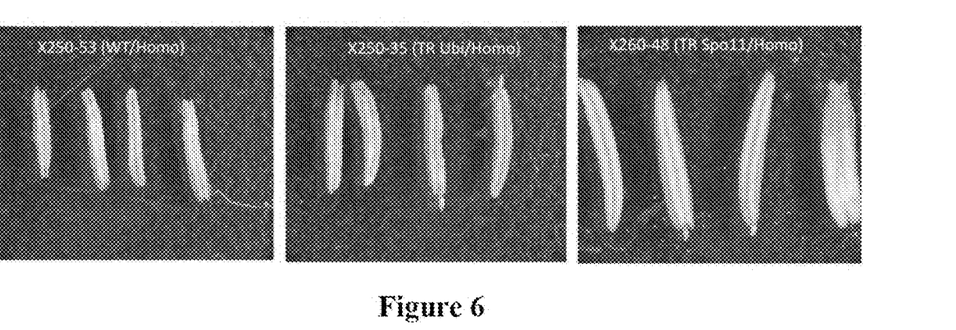
FIG. 6: Anthers. Anthers of homozygous mutant Zmspo11-1 (WT/Homo) plants supplemented by transgene L1605 (TR Spo11/Homo) or transgene L1604 (TR Ubi/Homo).
Figure 7:
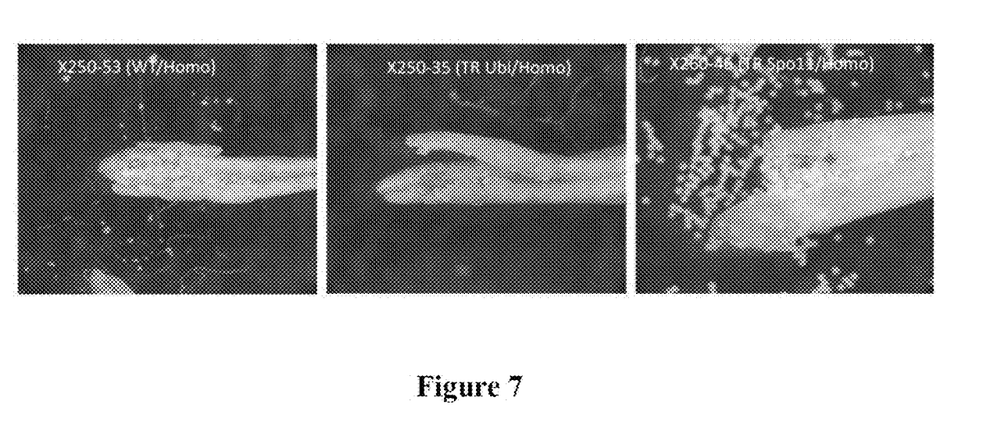
FIG. 7: Pollen. Pollen from the anthers of homozygous mutant Zmspo11-1 (WT/Homo) plants supplemented by transgene L1605 (TR Spo11/Homo) or transgene L1604 (TR Ubi/Homo).

The results of this analysis are presented in FIGS. 5 to 7 and show that
- the panicles of homozygous mutant plants complemented with transgene L1605 (ZmSpo11-1 promoter-TAL-ZmSpo11-1 fusion protein) carry a normal number of anthers, whereas complementation with transgene L1604 (ZmUBI promoter-TAL-ZmSpo11-1 fusion protein) only slightly increases the number of anthers of the mutant (WT/Homo),
- the anthers of homozygous mutant plants without complementation (WT/Homo) or complemented with L1604 (ZmUBI promoter-TAL-ZmSpo11-1 fusion protein) are atrophied, while the anthers complemented with L1605 (ZmSpo11-1 promoter-TAL-ZmSpo11-1 fusion protein) are normal (turgid),
- the anthers of homozygous mutant plants without complementation (WT/Homo) or complemented with L1604 (ZmUBI promoter-TAL-ZmSpo11-1 fusion protein) contain many aborted pollen grains and almost no turgid pollen grains, while the anthers complemented with L1605 (ZmSpo11-1 promoter-TAL-ZmSpo11-1 fusion protein) contain normal amounts of turgid pollen.

The Spo11-1 gene is recognized in many eukaryotic species as essential for meiotic recombination (Grelon et al. EMBO J. 2001 Feb. 1; 20(3):589-600; Stacey et al. Plant J. 2006 October; 48(2):206-16) and the SPO11-1 protein as necessary to initiate recombination by double-stranded DNA cleavage (Shingu et al. FEBS J. 2010 May; 277(10): 2360-74; Hartung et al. Plant Cell. 2007 October; 19(10): 3090-9) in a protein complex formed with SPO11-2 and TOPOVIB (Vrielynck et al. Science. 2016 Feb. 26; 351 (6276):939-43). Spo11-1 mutants are characterized by aberrations of meiosis leading to sterility. The fact that a TAL-ZmSpo11-1 fusion protein under the control of a promoter according to the invention present in plasmid L1605 complements the Zmspo11-1 mutation, demonstrates that this promoter is a promoter that is functional during meiosis. Furthermore, the results obtained also show that this promoter makes it possible to obtain a higher level of expression during meiosis than that obtained with a strong constitutive promoter such as the ubiquitin promoter.

SEQUENCE LISTING

```
<160> NUMBER OF SEQ ID NOS: 8

<210> SEQ ID NO 1
<211> LENGTH: 176
<212> TYPE: DNA
<213> ORGANISM: Zea mays

<400> SEQUENCE: 1
tgtattctct tcttgagggc aatttacgcc tcttgagaag ggtggcttcg ttgttgggct     60
cttgaaggcc cacgcagtcc aacggagccc actaagccta attctgtttc ttcgcgatcg    120
attagctgat tagctccatg gcggcttcga aaaaatcaaa ataaaaaact agcgcc        176

<210> SEQ ID NO 2
<211> LENGTH: 435
<212> TYPE: DNA
<213> ORGANISM: Zea mays

<400> SEQUENCE: 2
cactgatgct cctggaactg cagtgacggt tcggccgtgt caaattctcg ggtgtagggt     60
gtacctctgg ccaagtgact gatattctga aaaacatacg gacttctagt ataggagaag   120
aggaatccta atcctagtaa ttatatctta gtagatatgt gcttagtctc ttgttaattt    180
tttgtcttga gaggactata tatactgata aagtgataat ttattcagag aataaagaat   240
gggctccatg ctttgtctat gtattctctt cttgagggca atttacgcct cttgagaagg   300
gtggcttcgt tgttgggctc ttgaaggccc acgcagtcca acggagccca ctaagcctaa   360
ttctgtttct tcgcgatcga ttagctgatt agctccatgg cggcttcgaa aaaatcaaaa   420
taaaaaacta gcgcc                                                    435

<210> SEQ ID NO 3
<211> LENGTH: 673
<212> TYPE: DNA
<213> ORGANISM: Zea mays

<400> SEQUENCE: 3
```

```
gattgtccat ccagctccag gcgttccaga ggccctgata caggagatgt tccagcacaa      60 cccagggtg tccagggagg gtctcggcct gtacataagc cagaagctgg tgaaaacgat      120
gagcggcacg ttgcagtacc tacgagaagc cgacacctct tcgttcatca tcctgataga    180
gttcccggtc gcccagctca gcagcaagcg gtccaagcct tcgccaagta aattctgaca    240
ctgatgctcc tggaactgca gtgacggttc ggccgtgtca aattctcggg tgtagggtgt    300
acctctggcc aagtgactga tattctgaaa aacatacgga cttctagtat aggagaagag    360
gaatcctaat cctagtaatt atatcttagt agatatgtgc ttagtctctt gttaattttt    420
tgtcttgaga ggactatata tactgataaa gtgataattt attcagagaa taagaatgg    480 gctccatgct ttgtctatgt attctcttct tgagggcaat ttacgcctct tgagaagggt    540
ggcttcgttg ttgggctctt gaaggcccac gcagtccaac ggagcccact aagcctaatt    600
ctgtttcttc gcgatcgatt agctgattag ctccatggcg gcttcgaaaa aatcaaaata    660
aaaaactagc gcc                                                        673

<210> SEQ ID NO 4
<211> LENGTH: 1266
<212> TYPE: DNA
<213> ORGANISM: Zea mays

<400> SEQUENCE: 4
ctcatcttgg tctttcgata gctgttcttg aactgaaagg atgatttgac aaataagtga    60
actactaaat tgtacatcta gtttctatta actcagcaca actccaacat ttgtctcttg    120
taaataactt tcgcagtgct cctaattgtg ttagttataa tccacgaaaa ggattgtatg    180
ttgacaagga acagataaga cctaatgcta gcaaattcac ttctgaacat cttaactcct    240
aaaaaaaatt cgaccttctc acgtaggtca agaaaaccct gaaccctgt cacatccata     300 caaagtgata ttatagccca tgtgagaacg accgggaccg gtccttagac ctctgcttac    360
tcagcttaaa attcgctccc acgaggagtc gaatctatcc tggtcactgc accagccaag    420
atgcagtgat acatgtcact tcaggcatgt agttacactt gcagtttga acaatggaa     480 atgatccctg tgtaaaattg gcgctatccc tgccattcta tatacactgc aatgtggcga    540
atgcgagtat tggtggtgat gggagctgtg taactgattg actcaatgtg caggattgtc    600
catccagctc caggcgttcc agaggccctg atacaggaga tgttccagca aacccaggg    660 gtgtccaggg agggtctcgg cctgtacata agccagaagc tggtgaaaac gatgagcggc    720
acgttgcagt acctacgaga agccgacacc tcttcgttca tcatcctgat agagttcccg    780
gtcgcccagc tcagcagcaa gcggtccaag ccttcgccaa gtaaattctg acactgatgc    840
tcctggaact gcagtgacgg ttcggccgtg tcaaattctc gggtgtaggg tgtacctctg    900
gccaagtgac tgatattctg aaaaacatac ggacttctag tataggagaa gaggaatcct    960
aatcctagta attatatctt agtagatatg tgcttagtct cttgttaatt ttttgtcttg   1020
agaggactat atatactgat aaagtgataa tttattcaga gaataaagaa tgggctccat   1080
gctttgtcta tgtattctct tcttgagggc aatttacgcc tcttgagaag ggtggcttcg   1140
ttgttgggct cttgaaggcc cacgcagtcc aacggagccc actaagccta attctgtttc   1200
ttcgcgatcg attagctgat tagctccatg gcggcttcga aaaatcaaa ataaaaaact   1260 agcgcc                                                             1266

<210> SEQ ID NO 5
```

Figure 1:
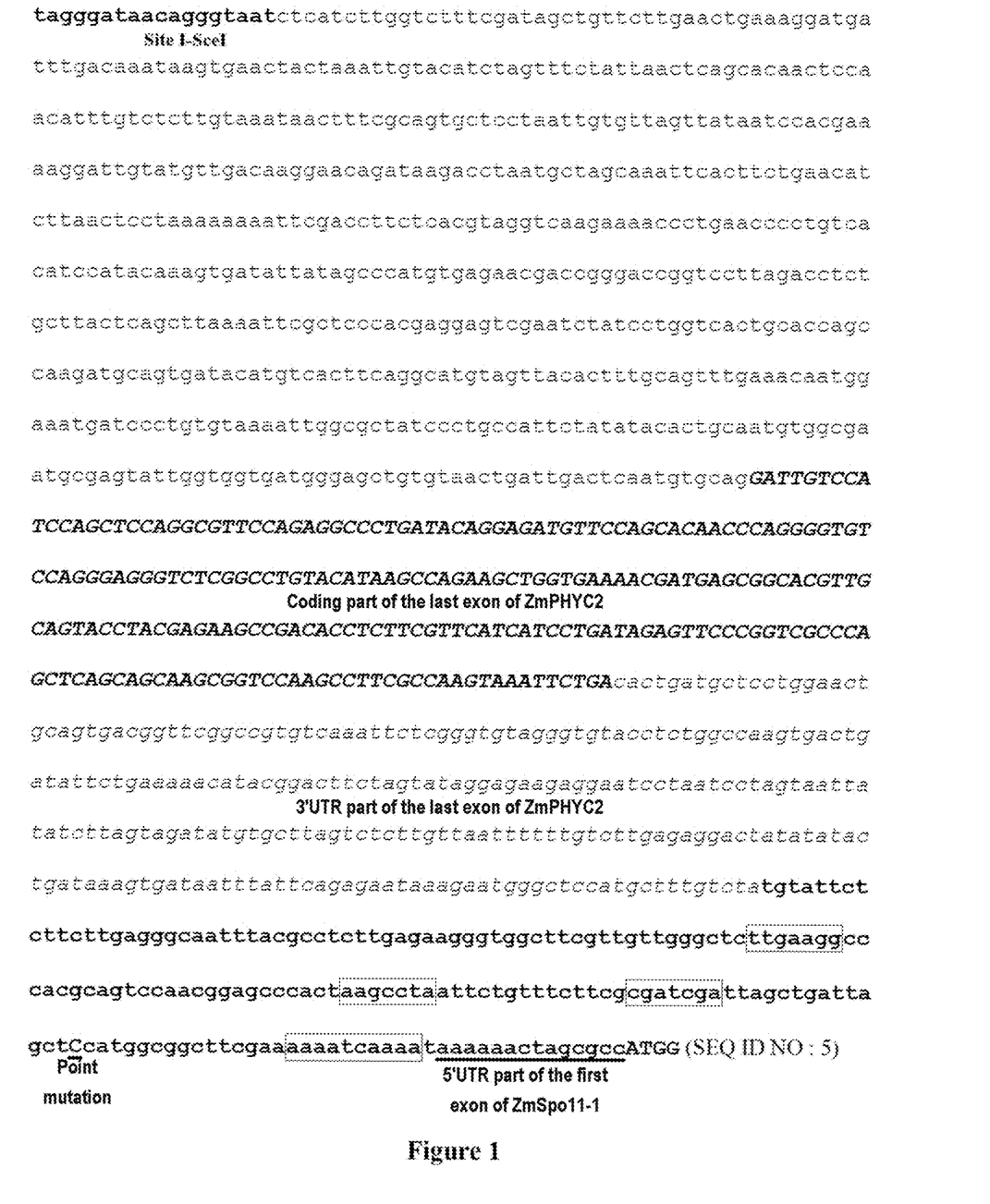
FIG. 1: Nucleotide sequence of the genomic region comprising the last intron, the last exon and the 3'UTR of the ZmPHYC2 gene and the intergenic region upstream of ZmSpo11-1. The framed sequences are conserved motifs in different species.

<211> LENGTH: 1288
<212> TYPE: DNA
<213> ORGANISM: Artificial Sequence
<220> FEATURE:
<223> OTHER INFORMATION: ZmSpo11-1 promoter region with point mutation to suppress NcoI restriction site (Figure 1)

<400> SEQUENCE: 5

```
tagggataac agggtaatct catcttggtc tttcgatagc tgttcttgaa ctgaaaggat    60
gatttgacaa ataagtgaac tactaaattg tacatctagt ttctattaac tcagcacaac   120
tccaacattt gtctcttgta ataactttc gcagtgctcc taattgtgtt agttataatc    180
cacgaaaagg attgtatgtt gacaaggaac agataagacc taatgctagc aaattcactt   240
ctgaacatct taactcctaa aaaaaattcg accttctcac gtaggtcaag aaaaccctga   300
acccctgtca catccataca aagtgatatt atagcccatg tgagaacgac cgggaccggt   360
ccttagacct ctgcttactc agcttaaaat tcgctcccac gaggagtcga atctatcctg   420
gtcactgcac cagccaagat gcagtgatac atgtcacttc aggcatgtag ttacactttg   480
cagtttgaaa caatggaaat gatccctgtg taaaattggc gctatccctg ccattctata   540
tacactgcaa tgtggcgaat gcgagtattg gtggtgatgg gagctgtgta actgattgac   600
tcaatgtgca ggattgtcca tccagctcca ggcgttccag aggccctgat acaggagatg   660
ttccagcaca acccaggggt gtccagggag ggtctcggcc tgtacataag ccagaagctg   720
gtgaaaacga tgagcggcac gttgcagtac ctacgagaag ccgacacctc ttcgttcatc   780
atcctgatag agttcccggt cgcccagctc agcagcaagc ggtccaagcc ttcgccaagt   840
aaattctgac actgatgctc ctggaactgc agtgacggtt cggccgtgtc aaattctcgg   900
gtgtagggtg tacctctggc caagtgactg atattctgaa aaacatacgg acttctagta   960
taggagaaga ggaatcctaa tcctagtaat tatatcttag tagatatgtg cttagtctct  1020
tgttaatttt ttgtcttgag aggactatat atactgataa agtgataatt tattcagaga  1080
ataaagaatg ggctccatgc tttgtctatg tattctcttc ttgagggcaa tttacgcctc  1140
ttgagaaggg tggcttcgtt gttgggctct tgaaggccca cgcagtccaa cggagcccac  1200
taagcctaat tctgtttctt cgcgatcgat tagctgatta gctgcatggc ggcttcgaaa  1260
aaatcaaaat aaaaaactag cgccatgg                                     1288
```

<210> SEQ ID NO 6
<211> LENGTH: 25
<212> TYPE: DNA
<213> ORGANISM: Artificial Sequence
<220> FEATURE:
<223> OTHER INFORMATION: Sequence recognized by TAL domain

<400> SEQUENCE: 6

```
tggttctgtg actacaagta caatg                                          25
```

<210> SEQ ID NO 7
<211> LENGTH: 10
<212> TYPE: DNA
<213> ORGANISM: Artificial Sequence
<220> FEATURE:
<223> OTHER INFORMATION: Conserved motif
<220> FEATURE:
<221> NAME/KEY: misc_feature
<222> LOCATION: (5)..(6)
<223> OTHER INFORMATION: n is a, c, g, or t

<400> SEQUENCE: 7

| | |
|---|---|
| aaaannaaaa | 10 |

```
<210> SEQ ID NO 8
<211> LENGTH: 10
<212> TYPE: DNA
<213> ORGANISM: Artificial Sequence
<220> FEATURE:
<223> OTHER INFORMATION: Conserved motif

<400> SEQUENCE: 8
```

| | |
|---|---|
| aaaatcaaaa | 10 |

The invention claimed is:

1. A process for expressing a coding sequence of interest in a plant cell during meiosis comprising introducing into said plant cell an expression cassette or an expression vector comprising a nucleic acid sequence which comprises a coding sequence of interest operably linked to a promoter having a functional transcriptional promoter activity during prophase I of meiosis, the promoter comprising a nucleotide sequence selected from the group consisting of (i) the nucleotide sequence as set forth in SEQ ID NO: 1, (ii) a nucleotide sequence having at least 98% nucleotide sequence identity to the nucleotide sequence as set forth in SEQ ID NO: 1, and (iii) a nucleotide sequence comprising a fragment of SEQ ID NO: 1 having at least 160 contiguous nucleotides of SEQ ID NO: 1, wherein said nucleotide sequence of (i), (ii) and (iii) have said functional transcriptional promoter activity during prophase I of meiosis, and wherein the nucleic acid sequence comprising the coding sequence of interest is heterologous with respect to said promoter.

2. The method according to claim 1, wherein said promoter having said functional transcriptional promoter activity during prophase I of meiosis comprises the nucleotide sequence as set forth in SEQ ID NO: 1 or has at least 99% nucleotide sequence identity to the nucleotide sequence as set forth in SEQ ID NO: 1.

3. The method according to claim 1, wherein said promoter having said functional transcriptional promoter activity during prophase I of meiosis is selected from the group consisting of the nucleotide sequence as set forth in SEQ ID NO: 1, SEQ ID NO: 2, SEQ ID NO: 3 and SEQ ID NO: 4.

4. The method according to claim 1, wherein said expression cassette comprising said nucleic acid sequence is introduced into said plant cell.

5. The method according to claim 1, wherein the coding sequence encodes a polypeptide of interest.

6. The method according to claim 1, wherein the coding sequence encodes an siRNA, an shRNA, an RNAi, an miRNA, an antisense RNA, a ribozyme, a DNAzyme or a guide RNA capable of targeting the action of a CRISPR-type endonuclease.

* * * * *